(12) United States Patent
Lee et al.

(10) Patent No.: US 8,783,494 B2
(45) Date of Patent: Jul. 22, 2014

(54) SHARPS CONTAINER (75) Inventors: Hoong Sim Lee, Singapore (SG);
Neville Chia, Singapore (SG)

(73) Assignee: Becton, Dickinson and Company,
Franklin Lakes, NJ (US)

( * ) Notice: Subject to any disclaimer, the term of this patent is extended or adjusted under 35 U.S.C. 154(b) by 0 days.

(21) Appl. No.: 13/808,349

(22) PCT Filed: Jul. 6, 2010

(86) PCT No.: PCT/SG2010/000254
§ 371 (c)(1),
(2), (4) Date: Jun. 17, 2013

(87) PCT Pub. No.: WO2012/005689
PCT Pub. Date: Jan. 12, 2012

(65) Prior Publication Data
US 2013/0256327 A1 Oct. 3, 2013

(51) Int. Cl.
*B65D 51/18* (2006.01)
*B65D 43/14* (2006.01)

(52) U.S. Cl.
USPC ...... 220/259.2; 220/213; 220/252; 220/259.1

(58) Field of Classification Search
USPC ............ 220/837, 213, 252, 259.1, 847, 259.2
See application file for complete search history.

(56) References Cited

U.S. PATENT DOCUMENTS

| | | | |
|---|---|---|---|
| 4,736,860 A * | 4/1988 | Bemis | 220/481 |
| 4,953,732 A | 9/1990 | Cocks | |
| 4,992,627 A * | 2/1991 | Mullaney | 174/41 |
| 5,076,429 A * | 12/1991 | Patrick et al. | 206/370 |
| 5,154,345 A | 10/1992 | Shillington et al. | |
| 5,178,322 A | 1/1993 | Shillington | |
| 5,387,735 A * | 2/1995 | Ponsi et al. | 588/249 |
| 5,413,243 A * | 5/1995 | Bemis et al. | 220/481 |
| 5,423,450 A * | 6/1995 | Shillington et al. | 220/481 |

(Continued)

FOREIGN PATENT DOCUMENTS

| WO | WO-96/31414 | 10/1996 |
|---|---|---|
| WO | WO-2005/120610 | 12/2005 |

OTHER PUBLICATIONS

"International Search Report of PCT/SG2010/000254", mailed on Sep. 29, 2010, 2 pages.

*Primary Examiner* — Mickey Yu
*Assistant Examiner* — Niki Eloshway
(74) *Attorney, Agent, or Firm* — Servilla Whitney LLC (57) ABSTRACT

A waste container (10) comprising a receptacle (11) and a closure (13) connectable to the receptacle (11). The closure (13) comprises a base (14) and a support (15) extending upwardly from the base (14). The support (15) defines a front opening (16) and having a rear wall (17). A tray (18) comprising a shelf (19) and an inferiorly depending guard (21) is also provided in the support (15), with the tray (18) being at least partially rotatable relative to the support (15). The closure (13) further comprises a shield (23) comprising a main body (24) extending from one edge (25) to a free edge (26) and having an upper surface (27) and a lower surface (28). The shield (23) is hingedly connected to the support (15) at or adjacent to the one edge (25) and is moveable between an open position in which it overlies the rear wall (17) of the closure (13) and a closed position in which it is secured to the closure (13) to at least substantially cover the front opening (16).

18 Claims, 8 Drawing Sheets

(56) References Cited

U.S. PATENT DOCUMENTS

| | | | |
|---|---|---|---|
| 5,494,186 A * | 2/1996 | Marsh | 220/481 |
| 5,740,909 A | 4/1998 | Nazare et al. | |
| 5,848,692 A | 12/1998 | Thorne et al. | |
| 6,250,465 B1 | 6/2001 | Daniels et al. | |
| 2010/0155400 A1 * | 6/2010 | Finnestad et al. | 220/200 |

* cited by examiner

SHARPS CONTAINER

FIELD OF THE INVENTION

The present disclosure relates to waste disposal containers including medical waste disposal containers.

BACKGROUND

With the risk of infection a key concern within the medical environment, it is important to provide safe and effective means to dispose of contaminated material such as syringes, other sharps, blood contaminated products and the like.

While containers have been developed for such purposes, there are a number of issues to address in order to achieve a safe and effective means of disposal. The opening of the container must be such that the material is properly received and does not fall out which is a problem with some current designs in which the opening is either too small or not suitably positioned to allow a user to partially insert a waste tray. Additionally, existing containers may not be suitably tamper-proof and/or do not properly prevent a user inserting their hand or at least their fingers through the opening and into the receptacle housing the contaminated products.

Existing containers may also not provide a final closure which securely covers the opening for waste. Even if provided, these final closures often interfere with the insertion of waste into the opening while the container is in use.

SUMMARY

In one aspect, there is provided:
a waste container comprising:
  a receptacle having a base wall, a side wall extending upwardly therefrom, said side wall defining an aperture in said receptacle;
  a closure connectable to said receptacle, said closure comprising:
  a base;
  a support extending upwardly from said base, said support defining a front opening and having a rear wall;
  a tray comprising a shelf and an inferiorly depending guard, wherein the tray is at least partially rotatable relative to the support; and
  a shield comprising a main body extending from one edge to a free edge and having an upper and a lower surface, said shield hingedly connected to said support at or adjacent to said one edge and moveable between an open position in which it overlies said rear wall of the closure and a closed position in which it is secured to said closure to at least substantially cover said front opening,
  said shield being hingedly connected to said support by a flexible hinge and moveable between the open and closed positions about said flexible hinge;
  and further wherein any relative rotatable movement of the tray is independent of movement of the shield between said open and closed positions.

In a second aspect, there is provided a closure for a waste container, said closure comprising:
  a base;
  a support extending upwardly from said base, said support defining a front opening and having a rear wall;
  a tray comprising a shelf and an inferiorly depending guard, wherein the tray is at least partially rotatable relative to the support; and
  a shield comprising a main body extending from one edge to a free edge and having an upper and a lower surface, said shield hingedly connected to said support at or adjacent to said one edge and moveable between an open position in which it overlies said rear wall of the closure and a closed position in which it is secured to said closure to at least substantially cover said front opening,
  said shield being hingedly connected to said support by a flexible hinge and moveable between the open and closed positions about said flexible hinge;
  and further wherein any relative rotatable movement of the tray is independent of movement of the shield between said open and closed positions.

DESCRIPTION OF EXEMPLARY EMBODIMENTS

The waste container may be used to collect a range of waste material which may include medical waste. Examples include syringes, other types of sharps, cannula ports, tubing, and/or materials contaminated by blood, or other bodily fluids or tissues.

The base of said closure typically comprises a rim around its periphery to relatively receive at least an upper part or upper edge of the receptacle therein. The rim comprises a first component, a second component and two opposing lateral components extending between the first and second components. In one embodiment, the first and second components are parallel. In addition or otherwise, the two opposed lateral components can be parallel.

The receptacle and the closure are connectable and preferably securely connectable to one another. While such securement may be achieved through a number of different arrangements, in one embodiment, the receptacle comprises a number of protrusions in said side wall. An outer wall of the rim of the base may comprise one or more complementary apertures to relatively receive said protrusions. In this embodiment, at least part of the outer wall of the rim of the closure is sufficiently substantially resiliently flexible such that the rim may be positioned over the upper edge of the receptacle and relatively lowered over the upper part of the receptacle such that the protrusions are relatively received within said apertures.

To ensure that the closure is correctly positioned on the receptacle, the receptacle may comprise a first number of protrusions along one sidewall and a second, different number of protrusions along the opposing sidewall. The closure, likewise, may have different numbers of apertures in opposing sides of said rim. The number of apertures along one side of the rim is equal to the number of protrusions along one sidewall of the receptacle and, likewise, for the other side of the rim and the other sidewall of the receptacle. Accordingly, this forces a user to put the closure on the receptacle in the correct orientation.

One, some or all of the protrusions preferably comprise an upper sloped surface extending from the side wall of the receptacle. The sloped surface may extend to a flattened apex. The apex is typically flattened to provide a relatively planar surface which is substantially parallel with the longitudinal axis of the receptacle. As such, a lower edge of the rim is relatively slidable along said upper sloped surface when a relatively downward force is exerted upon said rim. As the lower edge of the rim moves beyond the upper sloped face, the engagement between protrusion and rim ceases and the outer wall of the rim resiliently flexes or snaps back towards or against the side wall of the receptacle. Each of the complementary apertures are sized such that as the lower edge of the rim snaps back towards or against the side wall of the receptacle, the protrusion is housed within the aperture and preferably protrudes therethrough. Removal of the closure from the receptacle would be unlikely and would require a user to deliberately distort the outer wall of the rim and lift it over each of the protrusions.

The closure extends upwardly from said base and typically comprises a pair of shoulders. Each shoulder extends from or adjacent the first component of the rim towards the second component of the rim. The pair of shoulders may be opposed relative to one another and can be parallel. Each shoulder may extend upwardly relative to said base from a lower end to an apical region.

Each shoulder may comprise a front face portion and a rear face portion, with these portions connected laterally by a sidewall. The sidewalls of the shoulders are typically substantially parallel with each other and with the lateral components of the rim.

The respective front face portions of the shoulders typically define part of the front opening of the closure and the sidewalls of each shoulder typically form the lateral boundary of said opening.

Said rear wall of the closure extends between said rear face portions of the opposed and laterally disposed shoulders and thereby defines the rear boundary of the opening. The rear wall extends from an upper edge typically extending between said apical regions of the opposed shoulders to a lower edge, with said lower edge being connectable or connected to the base. In a preferred embodiment, said lower edge and said base are uniformly formed.

The rear wall typically comprises one or more connection members to connect said rear wall to said shield, for example, when said shield overlies said rear wall.

In one embodiment, the flexible hinge can be formed in the main body of the shield at or adjacent said one edge of said shield. The one edge of the shield can be connected to the rear wall. In this embodiment, the rear wall comprises a plurality of openings formed adjacent to said upper edge of the rear wall. Said openings are configured to receive and hold therein, shield tab members of the shield. Furthermore, the rear wall may further include retaining tabs which each depend from a first end connected to or integral with said rear wall and through at least part of said apertures to a free end. The shield tabs may be made from a relatively harder material than the retaining tabs of the rear wall so that, as the shield tabs are inserted through the openings, they cause the retaining tabs to flex to thereby accommodate the shield tabs in the openings.

The shield tabs typically comprise an elongate body extending from a fixed end, connected to or integral with the main body of the shield, to a free end. A portion of the shield tabs adjacent the free ends may have an increased diameter relative to the remainder of the tab. In one embodiment, the free end may form a hook or a flange component.

The shield tabs adjacent the one edge of the main body of the shield are extendible through the openings of the rear wall as described above. The retaining tabs of the rear wall are sufficiently substantially resiliently flexible such that they are each flexed by the shield tab to allow it to pass through the opening. Because the free ends of the shield tabs typically have a greater diameter than the remainder of the shield tab, said increased diameter causes a greater force against the retaining tab thus causing it to flex to a greater extent and allow passage of the retaining tab through the opening. The shield tabs lock in place within the opening when the hook or flange of the shield tab travels beyond the free end of the retaining tab. The abutment of retaining tab free end and the hook or flange typically holds the shield tab within the opening.

With the shield being lockable in place overlying the rear wall of the closure, the device provides a low profile closure for packaging. Furthermore the rear wall may be relatively concave such that the shield, when connected to the rear wall, is slightly recessed from the shoulders of the closure. Such features advantageously protect the shield from damage with the shoulders taking the brunt of any blows to the closure. This is important as if the shield was damaged and thus not able to close, the waste container immediately becomes a hazard on the basis that it is filled with contaminated and/or sharp objects.

The closure can further comprise a handle. The handle can extend from the first component of the rim of the closure. It can be substantially U-shaped. Initially, the handle can extend outwardly from the first component, for example at or about 90°. In use, the handle can be movable relatively downwardly about its join with the first component and be clipped by frictional engagement to the outer wall of the receptacle. In one embodiment, the handle after being moved can frictionally engage with a complementary protrusion member or members formed on the outer surface of the receptacle.

DETAILED DESCRIPTION OF THE DRAWINGS

One embodiment of a waste container 10 is shown in the accompanying drawings. The waste container 10 comprises various parts including a receptacle 11 having a flat base wall (not visible) and a side wall 12 extending upwardly from the base wall. The base wall and side wall can be formed as one part from one or more suitable materials, for example, a plastics material. The depicted receptacle is substantially rectangular in cross-section, however, it will be appreciated that the receptacle could have other cross-sectional shapes from that depicted.

The side wall defines an opening in the receptacle which again is not visible in the drawings due to the presence of the closure 13 that is securely connected to the top of the receptacle 11.

Closure 13 comprises a base 14 and a support 15 extending upwardly from the base. The support 15 defines a front opening 16 and further comprises a rear wall 17.

Tray 18 is counter-balanced and pivotally connected to support 15 and comprises a shelf 19 and a guard 21 which is positioned relatively inferior to said shelf 19.

When waste is placed on shelf 19, the weight of the waste causes relatively rearward rotation of the tray 18 around pivot pins 76 so leading to the waste being deposited into the receptacle 11. Such rotation of the tray 18 also exposes the guard 21 which acts as a barrier to block the front opening 16.

Closure 13 also comprises a shield 23 which has a main body 24 extending from one edge 25 to a free edge 26. The shield has an upper surface 27 and a lower surface 28. Shield 23 is connected to support 15 and is moveable between an open position in which it can be tethered to rear wall 17 of the closure and a closed position in which shield 23 covers opening 16.

Figure 6:
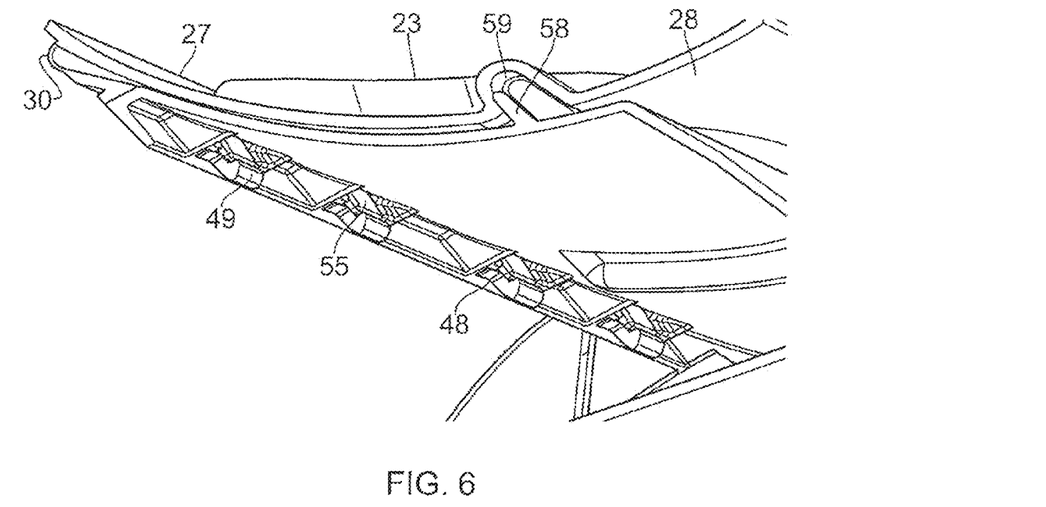
FIGS. 6 and 7 show perspective views of the shield and rear wall components of the waste container of FIG. 1.
Figure 7:
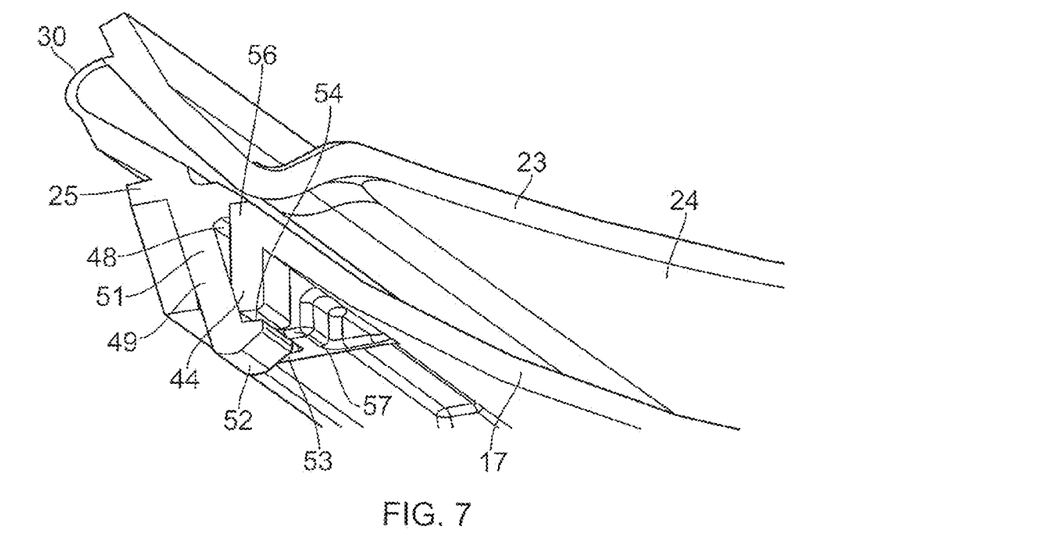

The movement of shield 23 is achieved by pivoting of the shield around flexible living hinge 30. As depicted in FIGS. 6 and 7, the living hinge 30 is formed in the main body 24 of the shield adjacent the one edge 25.

Base 14 comprises a rim 31 around its periphery to receive at least part of the receptacle 11 therein.

Side wall 12 of receptacle 11 comprises a plurality of substantially equally spaced and substantially horizontally disposed protrusions 35 which are relatively receivable within complementary apertures 37 of outer wall 36 of the rim 31.

Protrusions 35 each have an upper sloped surface 38 and extend substantially horizontally to an apex 39. As shown, the apex 39 is squared off or flattened to provide a relatively planar outer surface 41. As the closure 13 is relatively lowered over receptacle 11, edge 42 of rim 31 slides over upper sloped surfaces 38. The outer wall 36 is sufficiently resiliently flexible to flex out along the sloped surface 38 and over the protrusions 35. As the edge 42 moves beyond the respective upper sloped surfaces 38 and also beyond the planar apices 41, outer wall 36 of rim 31 resiliently snaps back against the sidewall of the receptacle such as to house the protrusions 35 within apertures 37. Protrusions 35 protrude through the apertures 37 when the closure 13 is locked in place onto receptacle 11.

Closure 13 also comprises a pair of shoulders 43. The pair of shoulders 43 are parallel and opposed relative to one another to define the lateral boundaries of opening 16.

Rear wall 17 extends between the shoulders 43 and defines a rear edge of opening 16. To this extent, rear wall 17 extends from an upper edge 44 to a lower edge 45 (see FIG. 8). Lower edge 45 and the base 14 are unitarily formed such that there is a relatively smooth join between the two.

Figure 1:
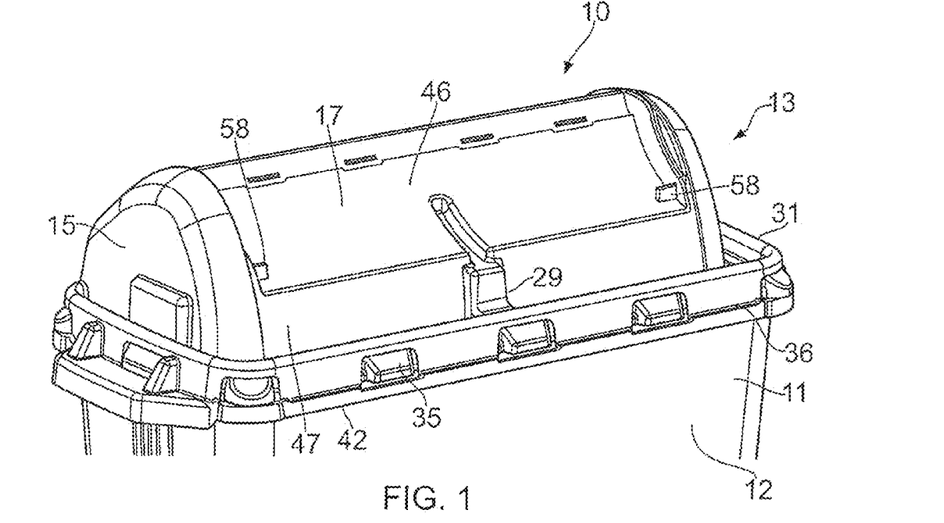
FIG. 1 is a rear perspective view of the upper portion of one embodiment of a waste container as described herein.

Rear wall 17 is also moulded as one piece with shoulders 43. Upper edge 44 spans shoulders 43 at a region close to the apex of each shoulder. Additionally, rear wall 17 comprises a concave portion 46 from which a planar portion 47 depends. Planar portion 47 extends from concave portion to the join of the rear wall 17 with base 14 and is essentially perpendicular to base 14. As shown in FIG. 1, there is a connection bar 29 molded between rear wall 17 and rim 31. Connection bar 29 adds to the strength of the closure along said rear portion.

Figure 2:
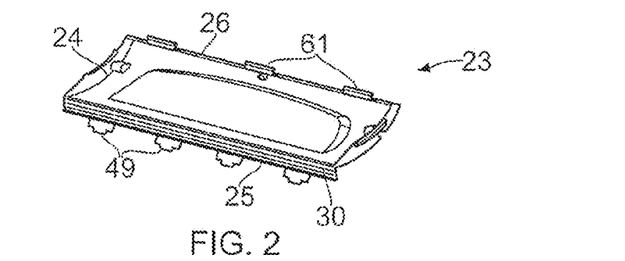
FIG. 2 is a perspective view of one embodiment of a shield prior to mounting to the waste container of FIG. 1.

Rear wall 17 comprises a series of apertures 48 adjacent upper edge 44. Apertures 48 relatively receive shield tabs 49. As can be seen in FIGS. 2, 6 and 7, shield tabs 49 comprise an elongate body 51 which extend from the one edge 25 of shield 23 to a free end 52. Free end 52 comprises a latch or hook component 53 which extends from the elongate body 51 to provide an area of increased diameter of shield tab 49. The latch component 53 comprises a cam surface 54 for abutment with a depending tab 55 of rear wall 17.

Depending tabs 55 each depend from a first end 56 connected to or integral with rear wall 17 to an engagement end 57.

Shield 23 and rear wall 17 are connected together through engagement of cam surface 54 with engagement end 57 of depending tab 55. Such interconnection allows a snap-fit arrangement of shield 23 to rear wall 17.

Shield 23 extends from the one edge 25 (connected to the rear wall as described above) to free edge 26. Living hinge 30 is located adjacent one edge 25. FIG. 7 shows the shield 23 in its open position where it depends from one edge 25 and overlies rear wall 17 to free edge 26 (visible in FIG. 2). Shield 23 is held in this open position by accommodation of retaining tab 58 on said rear wall 17 relatively within receiving recess 59 formed in lower surface 28 of shield 23. While the engagement of retaining tab 58 in receiving recess 59 is sufficient to hold the shield against the rear wall during use, the engagement may be overcome and the shield released from the rear wall by a user simply lifting the shield 23 away from the rear wall 17.

Figure 11A:
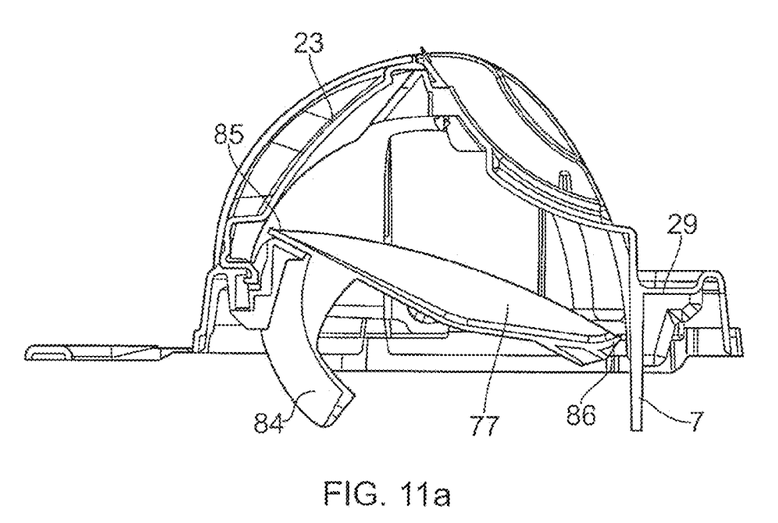
FIGS. 11a and 11b are cut away side elevational views showing the interior of the closure of the waste container and the movement of the tray of the closure.
Figure 11B:
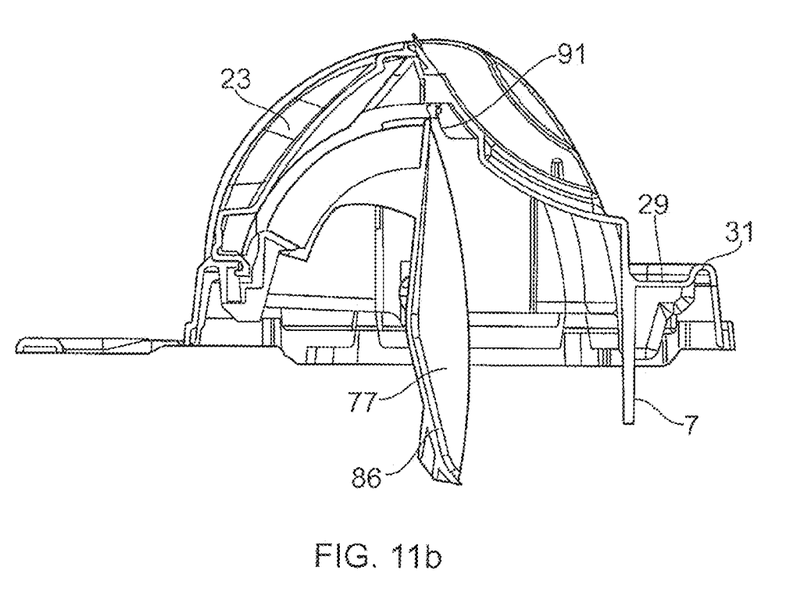

Once the engagement between the receiving tab 58 and retaining recess 59 is released, the shield 23 can be pivoted about living hinge 30 and towards the closed position wherein shield 23 covers front opening 16 as seen in FIGS. 11a and 11b.

Figure 4:
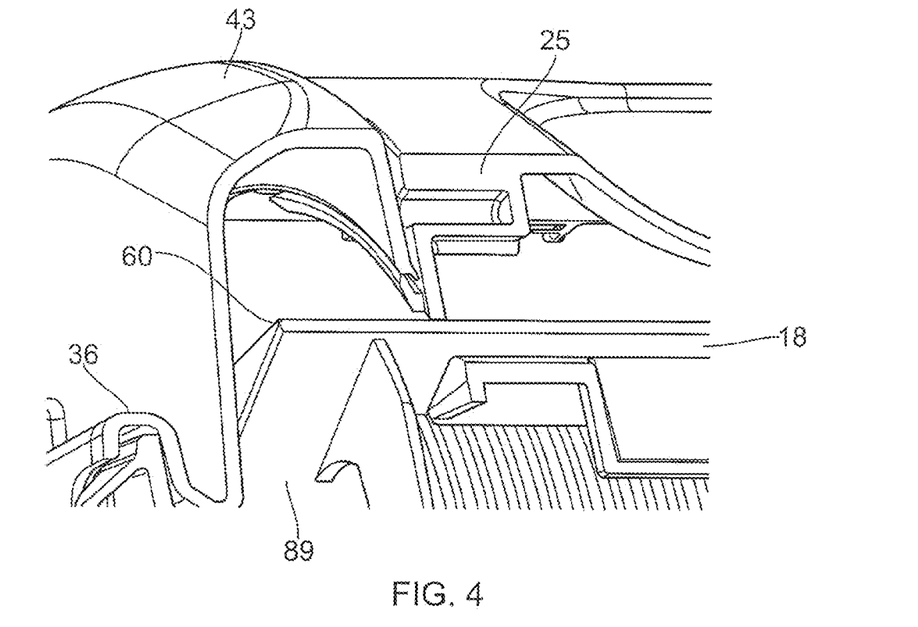
FIG. 4 is a partial perspective, partial cross-sectional view of one of the shoulder regions of the waste container of FIG. 1.

Shield 23 further includes two opposed lips 60 (see FIG. 4) which project laterally from the shield 23. Lips 60 are substantially arcuate and engage a complementary surface of the shoulders 43. This engagement between lips 60 and shoulders 43 further stabilises and secures the shield 43 in relation to the support, particularly as the shield is moved between its open and closed positions.

Figure 8:
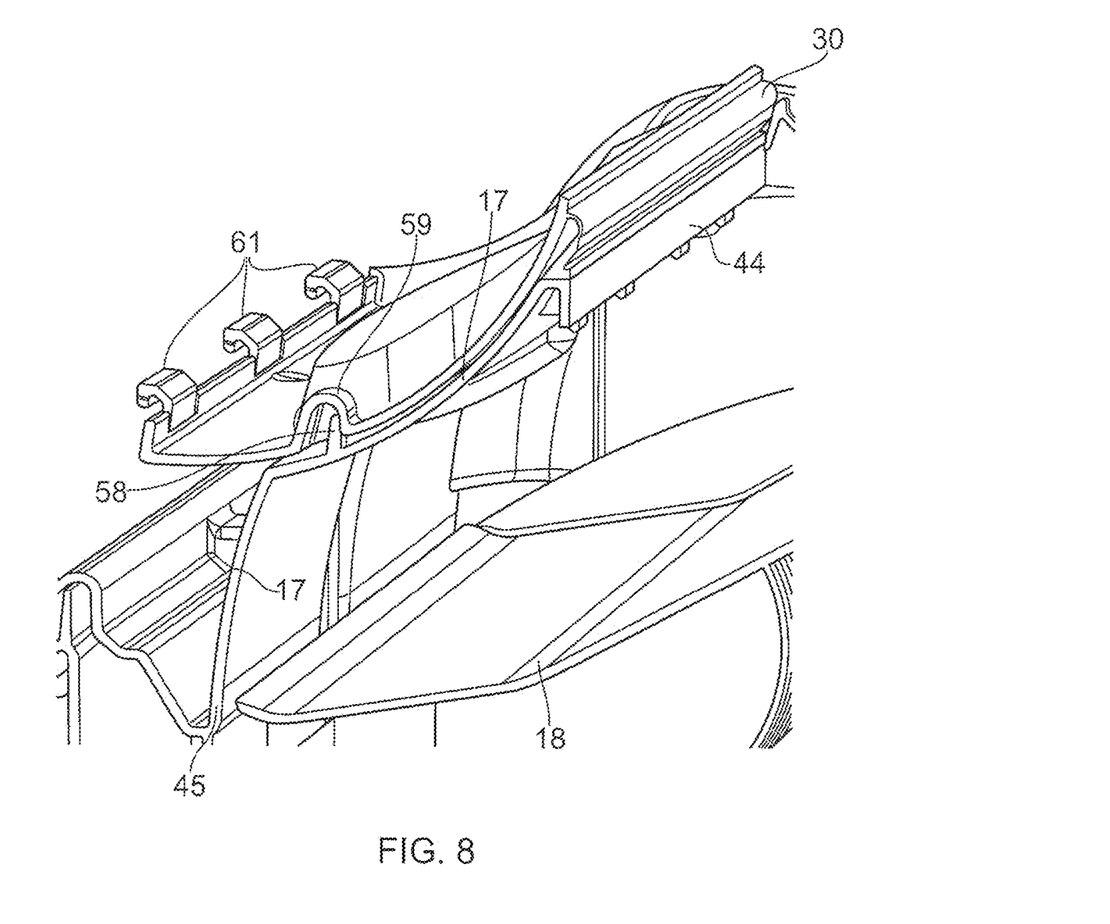
FIG. 8 is a side, partially cut away perspective view of the closure of the waste container of FIG. 1, with the shield shown in an open position.
Figure 9:
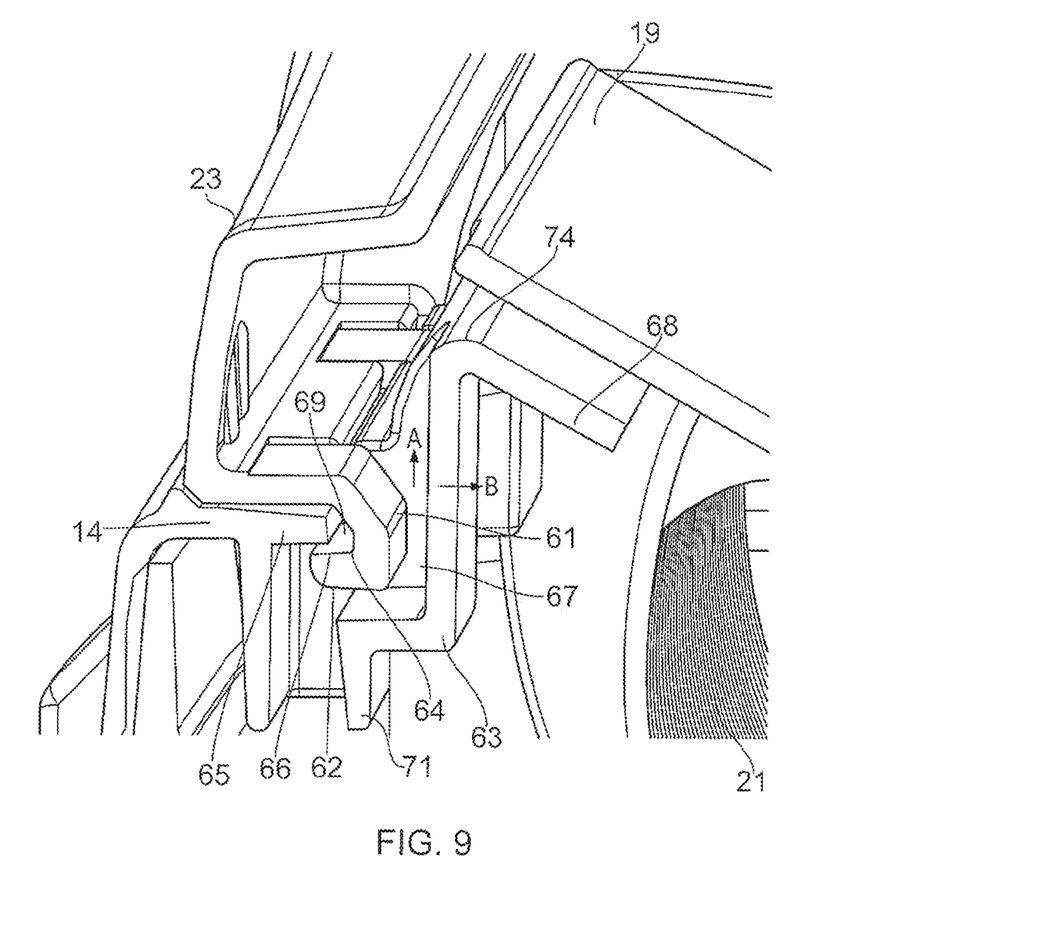
FIG. 9 is a partially cut away sectional view of the connection between the shield and the support when the shield of the waste container is in a final closed position.

Shield 23 comprises snap fit tabs 61 which extend from free edge 26. Snap fit tabs 61 are relatively received in complementary snap fit notches 62 of the support 15. Said snap fit notches 62 are formed between base 14 and a proximal wall 63 of support 15. As shown in FIGS. 8 and 9, the snap fit tabs 61 form hooked ends 64 which engage with flanges 65 which extend from base 14 into snap fit notches 62. The flanges 65 and hooked ends 64 may be in engagement or, as shown in FIG. 9, the flanges 65 may extend into a U-shaped recess 69 formed by the hooked ends 64. In this case, release of shield 23 from proximal wall 63 is not possible by simply lifting the shield upwardly as depicted by arrow A as such lifting would bring shoulder 66 of hooked end 64 into abutment with the underside of flange 65.

Proximal wall 63 extends from a first end 71 (adjacent one shoulder 43) to a second end 72 (adjacent the other shoulder 43) to define a front boundary of opening 16 spanning between shoulders 43. Proximal wall 63 extends upwardly for a height sufficient to provide said snap fit notches 62 whilst not occluding the opening to the extent that disposal of waste would be compromised.

Figure 10:
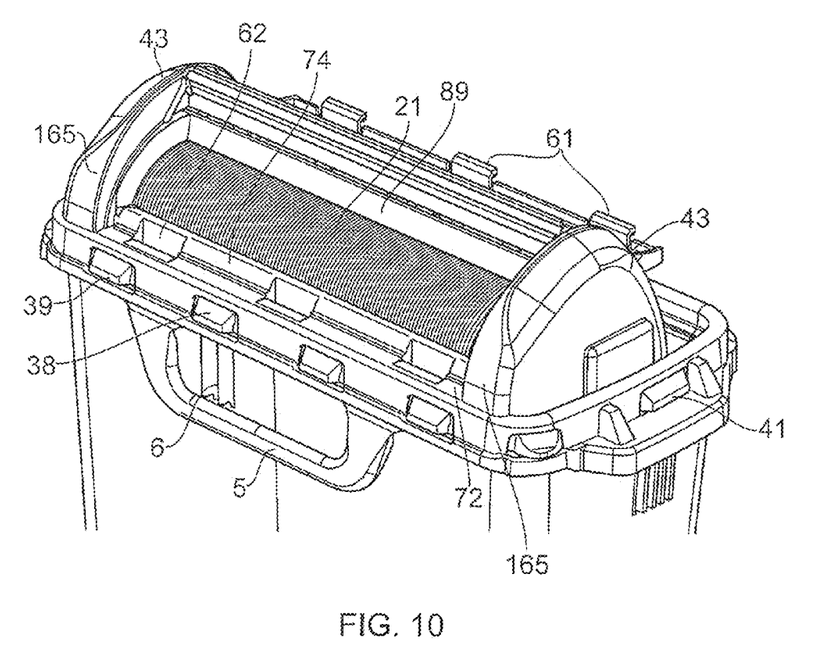
FIG. 10 is a front perspective view of the waste container of FIG. 1, with the tray depicted in a tilted configuration.

Proximal wall 63 (see FIG. 9) does not extend beyond proximal face 165 of each shoulder 43 (as shown in FIG. 10). In this way, the connection area of shield 23 and support 15 is protected against damage when shield 23 is closed and snap-fitted over the opening 16 which in turn reduces the chance of inadvertent opening should the container 10 be subject to a knock or bang. Force applied to the closure will be typically cushioned by shoulders 43.

In addition to providing said snap fit notches 62, the proximal wall 63 comprises at least one inwardly sloping lip 68 extending from an upper edge 74. The sloping lip 68 is positioned at or adjacent either or both of the first end 71 or second end 72 of proximal wall 63 to provide a stopper for tray 18, that is, tray 18 abuts with the fixed sloping lip and cannot pivot proximally beyond said lip when in its waste receiving position.

Figure 3:
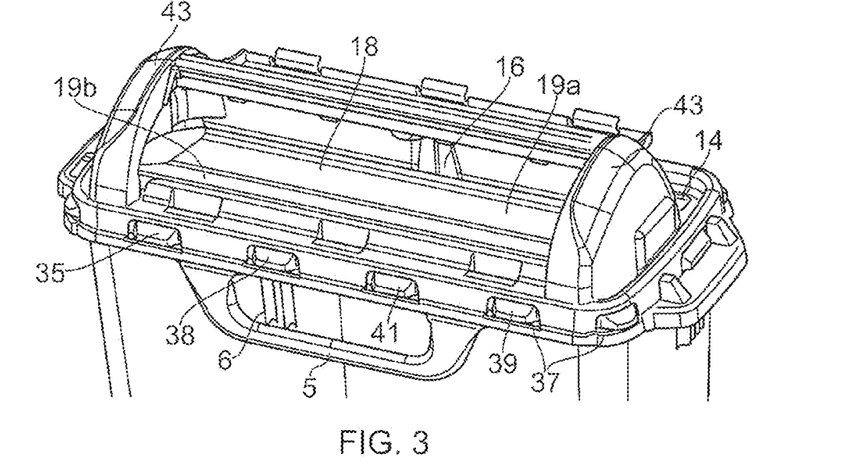
FIG. 3 is a front perspective view of the upper portion of the waste container of FIG. 1.

As depicted in FIGS. 3 and 10, the closure 10 further comprise a substantially U-shaped handle 5 that extends from the rim 31 of the closure 10. As depicted in FIGS. 11a and 11b, initially, the handle 5 can extend outwardly from the first component, for example at or about 90°. In use, the handle 5 can be movable relatively downwardly about its join with the rim 31 and be clipped by frictional engagement with the complementary protrusion members 6 formed on to the front of the side wall 12 of the receptacle 11.

Tray 18 is pivotally mounted within opening 16. As shown in, for example, FIG. 3, tray 18 is fully housed within shoulders 43.

Figure 12A:
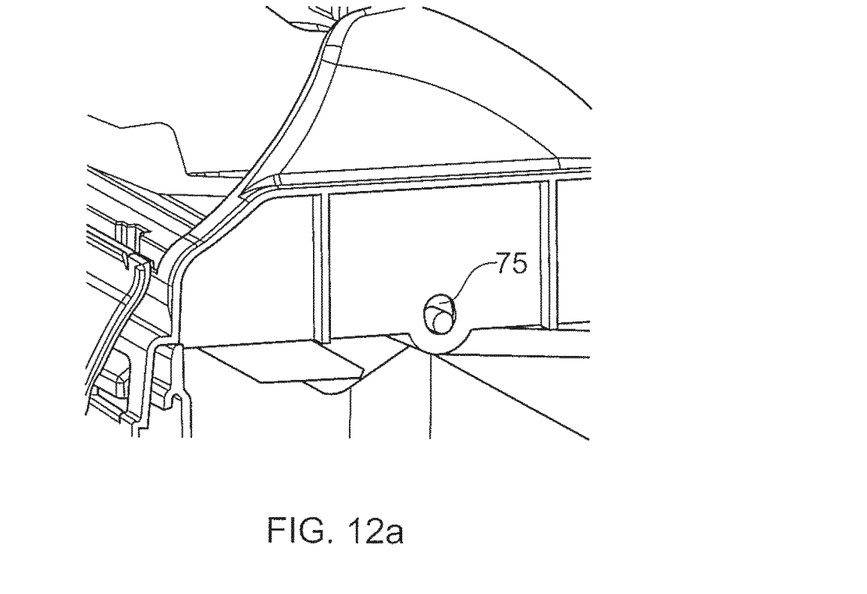
FIGS. 12a and 12b are, respectively a cut-away perspective view and enlarged view showing the location of the pivot points of the tray of the waste container.
Figure 12B:
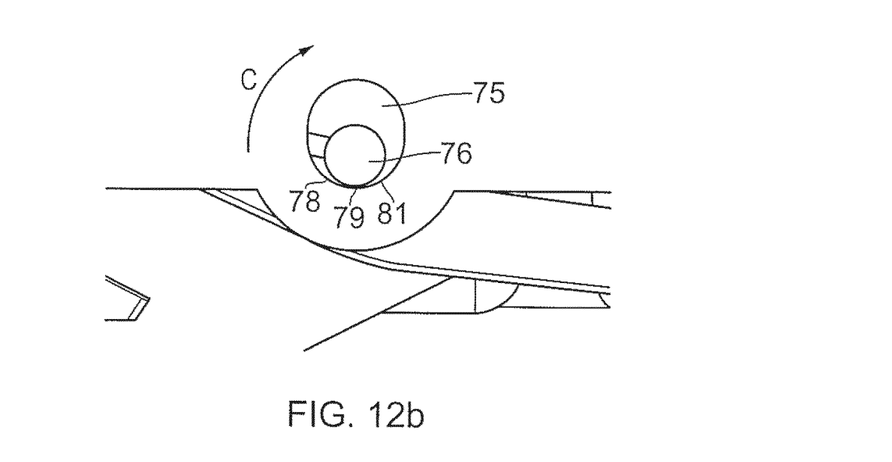

To improve waste, disposal success rate, the rotation of the tray 18 must be sensitive to the weight of waste placed thereon. To achieve this, shoulders 43 comprise opposed hinge apertures 75 (see FIGS. 12a and 12b) to receive pivot pins 76 which extend from sidewalls 77 of the tray 18. Pins 76 are substantially cylindrical and are configured to extend through said hinge apertures 75. The pins 76 roll within the hinge apertures 75 as waste is placed on tray 18 thus allowing the tray 18 to rotate relatively inwardly of the container 10 and for the waste to fall into receptacle 11. To further enhance the sensitivity of the tray rotation, hinge apertures 75 comprise a lower surface 78 which has a substantially flat base portion 79 extending to a second, sloped planar surface 81. As each pin 76 rolls within a corresponding hinge aperture 75 in the direction depicted by Arrow C (see FIG. 12b), the flat base 79 and the second sloped planar surface 81 act to reduce the contact of the pin 76 against said lower surface 78 of the aperture to thereby reduce friction and drag, which in turn increases the tray sensitivity to lighter wastes.

The design of the closure 10 is such that the tray cannot be readily disassembled once constructed. Particularly, it is evident from the Figures, pivot pins 76 are recessed within shoulders 43, making it almost impossible, if not impossible, for a user to introduce a hand or other object to disconnect said pivot pins 76 and release tray 18.

Tray 18 comprises two substantially planar shelf portions 19a, 19b, which are angled relative to one another. The tray 18 has a first edge 85, a second edge 86 and two side edges 77. Tray 18 has an upper surface 88 and a lower surface 89. Guard 21 depends from lower surface 89 at a region adjacent proximal edge 85. Guard 21 is dimensioned such that it does not span the entire underside of tray 18. Rather, the shelf portions 19a, 19b extend beyond the guard 21 at lateral regions 87a and 87b to form opposed abutment regions to abut with inwardly sloping lip 68 as described above.

Figure 5:
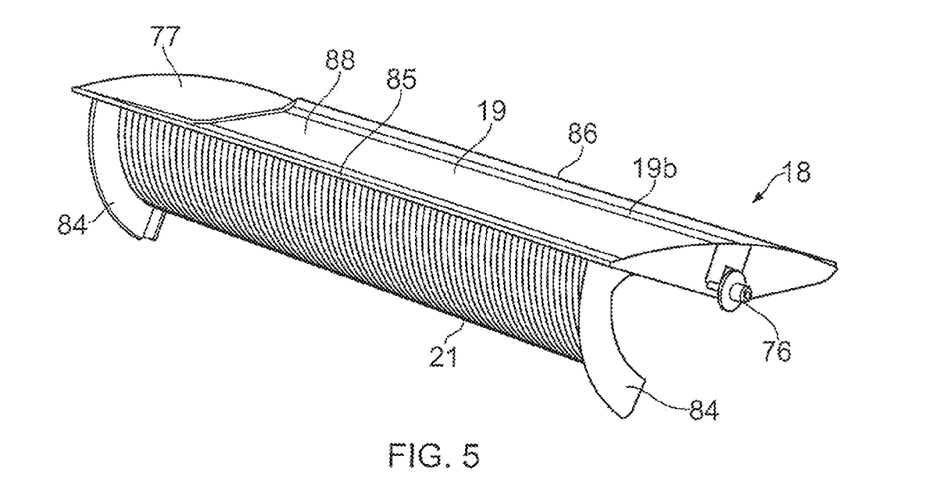
FIG. 5 is a perspective view of the tray depicted removed from the waste container of FIG. 1.

Guard 21 is a substantially arcuate and ribbed solid member with opposed side flanges 84 (see for example FIGS. 5 and 11a) which provide stability to tray 18.

As waste is placed on the shelf surface portions 19a, 19b, the weight of the waste causes tray 18 to pivot around pivot points 76 as described above. Tray 18 pivots in a direction towards rear wall 17 so causing the waste to slide off the tray through the gap created between the tray and the downwardly extending guard member 7 and so fall into receptacle 11 below. As tray 18 pivots it moves from a substantially receiving orientation to a depositing configuration as shown by comparing FIGS. 11a and 11b.

Tray 18 moves from a receiving configuration substantially perpendicular to the longitudinal axis of the container to a depositing configuration substantially parallel with axis. Movement beyond the depositing configuration of FIG. 11b is prevented by abutment of a region of first edge 85 with shoulder 91 formed on an inner surface of shoulders 43.

The counterbalance caused by the positioning of the guard 21 causes tray 18 to return to its first receiving configuration once the weight of the waste material is removed.

When receptacle 11 fills with waste, the waste will block the movement of the tray 18 in the full depositing configuration (FIG. 11b). At this stage, a user may release shield 23 from rear wall 17, and move it about its living hinge such that it covers opening 16. Shield 23 is then secured in place over opening 16 as discussed above.

The movement of tray 18 is entirely independent of the movement of shield 23.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A waste container comprising:
   a receptacle having a base wall, a side wall extending upwardly therefrom, said side wall defining an aperture in said receptacle;
   a closure connectable to said receptacle, said closure comprising:
   a base;
   a support extending upwardly from said base, said support defining a front opening and having a rear wall;
   a tray comprising a shelf and an inferiorly depending guard, wherein the tray is at least partially rotatable relative to the support about a first axis, and when the tray is in a rearward position the guard blocks the front opening;
   a shield comprising a main body extending from one edge to a free edge and having an upper and a lower surface, said shield hingedly connected to said support with a flexible hinge at or adjacent to said one edge at a second axis remote from the first axis, and pivotable between an open position in which the shield overlies said rear wall of the closure and a closed position in which it is secured to said closure to at least substantially cover said front opening;
   and further wherein any relative rotatable movement of the tray is independent of movement of the shield between said open and closed positions.

2. The waste container of claim 1 wherein the support extends upwardly from said base and comprises a pair of opposed parallel shoulders.

3. The waste container of claim 2 wherein the shoulders each have respective front face portions that define part of the front opening of the closure.

4. The waste container of claim 2 wherein said rear wall of the closure extends between rear face portions of the opposed shoulders and thereby defines the rear boundary of the opening.

5. The waste container of claim 2 wherein the rear wall is relatively concave.

6. The waste container of claim 2 wherein said tray is connected at least one connection to said shoulder, said connection being recessed in said shoulders.

7. The waste container of claim 1 wherein the rear wall comprises one or more connection members to connect said rear wall to said shield.

8. The waste container of claim 1 wherein the flexible hinge is formed in the main body of the shield at or adjacent said one edge of said shield.

9. The waste container of claim 8 wherein the one edge of the shield is connected to the rear wall and the rear wall comprises a plurality of openings formed adjacent to said upper edge of the rear wall, said openings being configured to receive and hold therein, shield tab members of the shield.

10. A closure for a waste container, said closure comprising:
- a base;
- a support extending upwardly from said base, said support defining a front opening and having a rear wall;
- a tray comprising a shelf and an inferiorly depending guard, wherein the tray is at least partially rotatable relative to the support about a first axis, and when the tray is in a rearward position the guard blocks the front opening;
- a shield comprising a main body extending from one edge to a free edge and having an upper and a lower surface, said shield hingedly connected to said support with a flexible hinge at or adjacent to said one edge at a second axis remote from the first axis, and pivotable between an open position in which the shield overlies said rear wall of the closure and a closed position in which it is secured to said closure to at least substantially cover said front opening;
- and further wherein any relative rotatable movement of the tray is independent of movement of the shield between said open and closed positions.

11. The closure of claim 10 wherein the support extends upwardly from said base and comprises a pair of opposed parallel shoulders.

12. The closure of claim 11 wherein the shoulders each have respective front face portions that define part of the front opening of the closure.

13. The closure of claim 11 wherein said rear wall of the closure extends between rear face portions of the opposed shoulders and thereby defines the rear boundary of the opening.

14. The closure of claim 11 wherein the rear wall is relatively concave.

15. The closure of claim 11 wherein said tray is connected at least one connection to said shoulder, said connection being recessed in said shoulders.

16. The closure of claim 10 wherein the rear wall comprises one or more connection members to connect said rear wall to said shield.

17. The closure of claim 10 wherein the flexible hinge is formed in the main body of the shield at or adjacent said one edge of said shield.

18. The closure of claim 17 wherein the one edge of the shield is connected to the rear wall and the rear wall comprises a plurality of openings formed adjacent to said upper edge of the rear wall, said openings being configured to receive and hold therein, shield tab members of the shield.

\* \* \* \* \*